(12) United States Patent
Bosshard et al.

(10) Patent No.: US 8,216,179 B2
(45) Date of Patent: Jul. 10, 2012

(54) BREASTPUMP SET

(75) Inventors: Patrik Bosshard, Buonas (CH); Beda Weber, Sins (CH); Charles Giezendanner, Morschach (CH)

(73) Assignee: Medela Holding AG, Baar (CH)

( * ) Notice: Subject to any disclaimer, the term of this patent is extended or adjusted under 35 U.S.C. 154(b) by 199 days.

(21) Appl. No.: 12/374,038

(22) PCT Filed: Jul. 10, 2007

(86) PCT No.: PCT/CH2007/000332
§ 371 (c)(1),
(2), (4) Date: Jan. 15, 2009

(87) PCT Pub. No.: WO2008/009145
PCT Pub. Date: Jan. 24, 2008

(65) Prior Publication Data
US 2010/0016789 A1   Jan. 21, 2010

(30) Foreign Application Priority Data

Jul. 18, 2006  (CH) .................................. 1156/06

(51) Int. Cl.
*A61M 1/06* (2006.01)
(52) U.S. Cl. ........................................ 604/74
(58) Field of Classification Search .............. 604/74, 604/75, 76
See application file for complete search history.

(56) References Cited

U.S. PATENT DOCUMENTS

| | | | |
|---|---|---|---|
| 4,813,932 A * | 3/1989 | Hobbs ............................ 604/74 |
| 5,542,921 A * | 8/1996 | Meyers et al. .................. 604/74 |
| 5,571,084 A * | 11/1996 | Palmer ............................ 604/74 |
| 6,004,288 A * | 12/1999 | Hochstedler et al. ........... 604/74 |
| 6,042,560 A * | 3/2000 | Niederberger .................. 604/74 |
| 6,109,100 A * | 8/2000 | Buckley et al. ................. 73/198 |
| 6,110,140 A * | 8/2000 | Silver ............................. 604/74 |
| 6,547,756 B1 | 4/2003 | Greter et al. |
| 6,673,036 B1 * | 1/2004 | Britto .............................. 604/74 |
| 6,706,012 B2 * | 3/2004 | McKendry et al. ............. 604/74 |
| 7,201,735 B2 * | 4/2007 | Atkin et al. ..................... 604/74 |
| 2002/0182584 A1 | 12/2002 | Morton |
| 2002/0193731 A1 * | 12/2002 | Myers et al. .................... 604/74 |
| 2003/0040734 A1 * | 2/2003 | Morton et al. ................. 604/514 |
| 2004/0024351 A1 * | 2/2004 | Greter et al. .................... 604/74 |
| 2005/0059928 A1 * | 3/2005 | Larsson ......................... 604/74 |
| 2005/0101908 A1 * | 5/2005 | Atkin et al. ..................... 604/74 |
| 2007/0219486 A1 * | 9/2007 | Myers et al. .................... 604/74 |
| 2008/0021380 A1 * | 1/2008 | Thommen ...................... 604/74 |
| 2008/0177224 A1 * | 7/2008 | Kelly et al. ..................... 604/74 |

FOREIGN PATENT DOCUMENTS

| | | |
|---|---|---|
| EP | 1502610 A1 | 2/2005 |
| WO | 00/41744 A1 | 7/2000 |
| WO | 03/066133 A1 | 8/2003 |
| WO | 2006/079229 A1 | 8/2006 |

* cited by examiner

*Primary Examiner* — Christopher D Koharski
*Assistant Examiner* — Aarti B Berdichevsky
(74) *Attorney, Agent, or Firm* — McDonnell Boehnen Hulbert & Berghoff LLP (57) ABSTRACT

A breastpump set for expressing human breastmilk comprises at least one breastshield (1) to be placed on a mother's breast with a coupling part (12) for connection to a milk collection container (2), and a suction pump unit (4) with an electrically operated suction pump, wherein the breastshield is provided with a signal transmission and/or reception unit (5) for transmitting signals to the suction pump unit (4), and the signal transmission unit comprises, for example, a programming device for manual or automatic programming of the suction pump unit. The breastpump set according to the invention make it easier for the mother to operate the pump and breastshield while expressing milk.

8 Claims, 6 Drawing Sheets

BREASTPUMP SET

TECHNICAL FIELD

The invention relates to a breastpump set, a breast shield, a suction tube, and a method for operating a breastpump set.

PRIOR ART

Breastpumps for expressing human breastmilk are well known. There are basically two different types. The first are operated manually, i.e. the vacuum needed to express milk is generated by manual actuation of the suction pump. In the second type, the suction pump is operated electrically, in which case the suction pump can be connected to the mains electricity and/or can be operated by a battery or another energy storage means.

To ensure that the function of the breastpump can be adapted optimally to the needs of the mother, some of the pumps allow the mother to regulate the vacuum. For example, U.S. 2004/0024351 and U.S. Pat. No. 4,813,932 disclose manually actuated breastpumps that have adjustable valves. In the case of manually operated pumps, the suction capacity of the pump itself is additionally regulated by means of the mother increasing or decreasing the pump strength to meet her requirements.

In electrically operated pumps too, it is customary for air release openings to be arranged on the breast shield or on the connecting line to the suction pump. This is the case in U.S. Pat. No. 6,706,012 and U.S. Pat. No. 6,042,560, for example.

U.S. Pat. No. 6,110,140 proposes a manually or electrically operated breastpump which, in the area of the breast shield, has a vacuum regulator for regulating the vacuum generated by the suction pump. This regulator can be actuated during use of the breastpump such that the vacuum in the breast shield can be adjusted.

In addition to the solutions described above, which all allow the vacuum generated by the suction pump to be modified in the area of the breast shield, some electrically operated breastpumps also afford the possibility of modifying the vacuum or the suction rhythm on the pump device itself. This is done via corresponding actuation switches or buttons that are arranged on the suction pump. However, to be able to actuate these buttons, the mother has to have one hand free. However, this is not possible, or is possible only with difficulty, if the mother wishes to express milk from both breasts simultaneously.

U.S. Pat. No. 6,547,756 discloses a programmable breastpump which, in accordance with various pump programs, can ensure that the suction capacity, and the pumping frequency as a function of time, are the best possible for the mother and for the baby. The programs are preferably downloaded from a computer into a memory unit of the pump and/or are loaded on a memory chip that can be read by the electronics of the pump.

EP 1 502 610 proposes combining a manually operated breastpump with an electronic breastpump. In the manual operation, the desired pump frequency is forwarded in a learning mode to the electronics of the electronic breastpump. Upon switching to automatic operation, the pump operates according to the values predefined in the learning mode.

WO 2005/070476 describes a breast shield insert which is designed to be fitted into a breast shield and which has integrated electrical heating elements. In this way, the breast shield can be warmed to a temperature that is comfortable for the mother.

WO 2003/066133 proposes a breast shield which is equipped at predefined locations with measurement electrodes. These electrodes are connected to an evaluation device, which can be integrated in the breastpump.

PCT application PCT/CH2005/000730 of Dec. 7, 2005, which is still to be published, further proposes that a breast shield be provided with operating means for operating the suction pump. In this way, the mother can influence the function of the suction pump during the expression of milk, without having to be able to reach the suction pump. To work the operating means, the mother can use the same hand with which she is holding the breast shield to her breast. This is particularly advantageous when expressing milk from both breasts simultaneously.

DISCLOSURE OF THE INVENTION

The object of the invention is therefore to allow the mother to express breastmilk as easily and yet as comfortably as possible.

This object is achieved by the breastpump set or system described in the present application.

According to the invention, the breast shield is provided with a transmitter and/or a receiver, such that the mother, while she is expressing milk, is able to trigger and/or control and/or monitor actions on the breast shield and/or to receive information. She does not need to have a hand free to do this, and instead she can use the hand that is holding the breast shield to her breast. Moreover, the breast shield can automatically transmit manually generated pumping procedures or modes to a memory or to a control device of a suction pump unit or to another storage medium.

The communication from the transmission unit and/or reception unit facing the breast shield is preferably wireless. The unidirectional or bidirectional communication is preferably established with a suction pump unit or with a control device of the suction pump. However, it can instead or in addition be established with a computer or another data processing device or also with the milk collection container. In the latter case, for example, a filling level sensor can be arranged in the milk collection container and sends information on the filling level to the receiver on the side of the breast shield and/or to the receiver at the suction pump. Furthermore, the receiver on the side of the breast shield can contain a radio clock or another time measurement by means of which the pump time is displayed. The clock time or the pump duration can also be transmitted as signal from the suction pump unit to the receiver on the side of the breast shield.

The wireless communication has the advantage that no connector plugs, connections or cables are needed, which can quickly become soiled and are difficult to clean. Furthermore, the production costs are thereby reduced, which is particularly relevant in the case of the breast shields which, for hygiene reasons, should be used only for a short time and only by one person.

In a preferred embodiment, the breastpump set according to the invention for expressing human breastmilk comprises at least one breast shield to be placed on a mother's breast with a coupling part for connection to a milk collection container, and a suction pump unit with an electrically operated suction pump, wherein on the side of the breast shield a signal transmission unit is provided for transmitting signals to the suction pump unit. According to the invention, this signal transmission unit comprises a programming device for manual or automatic programming of the suction pump unit.

In another preferred embodiment, the breastpump set according to the invention for expressing human breastmilk comprises at least one breast shield to be placed on a mother's breast with a coupling part for connection to a milk collection container, and a suction pump unit with an electrically operated suction pump, said breastpump set having two signal transmission units, of which a first signal transmission unit is provided on the side of the breast shield and a second signal transmission unit is provided on the side of the suction pump.

In another preferred embodiment, the breastpump set according to the invention for expressing human breastmilk comprises at least one breast shield to be placed on a mother's breast with a coupling part for connection to a milk collection container, and an electrically operated suction pump, wherein a signal reception unit is arranged in the area of the breast shield.

In the three embodiments described above, the signal transmission and/or reception unit on the side of the breast shield is preferably arranged on the breast shield, on a plug connection on the side of the breast shield for connecting the breast shield to a vacuum or suction tube, or on the vacuum tube itself.

Further advantageous embodiments are set forth in the dependent patent claims.

BRIEF DESCRIPTION OF THE DRAWINGS

The subject matter of the invention is explained below on the basis of preferred illustrative embodiments depicted in the attached drawings, in which.

WAYS OF IMPLEMENTING THE INVENTION

Figure 1:
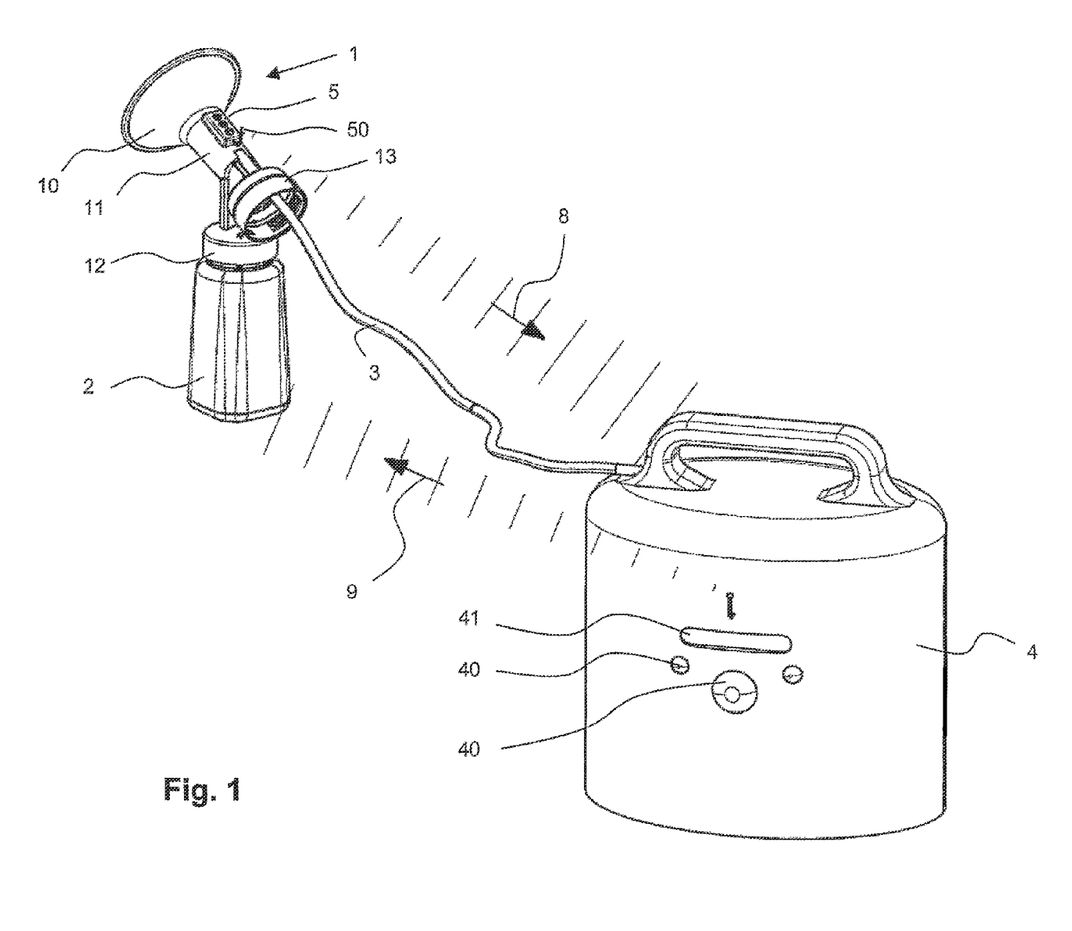
FIG. 1 shows a schematic view of a breastpump set according to a first embodiment of the invention.

FIG. 1 shows a first embodiment of the breastpump set or system according to the invention. It basically comprises at least one breast shield 1, a milk receiving or collection container 2 that can be secured on the breast shield 1, and a suction pump unit 4 with an electrically operated suction pump, which can be connected to the breast shield 1 via a suction line 3. The connection is preferably established using plug connections.

If two breast shields 1 are used in order to express milk from both breasts simultaneously, then two suction lines are present, which are attached to the same pump device.

The breast shield 1 has a breast shield funnel 10, which is placed on the mother's breast during use. The funnel 10 merges into a breast shield neck 11, which is adjoined by first and second breast shield coupling parts 12, 13. The first breast shield coupling part 12 has an inner thread that can be screwed onto an outer thread of the milk collection container 2, here a baby's bottle. The second breast shield coupling part 13 has an attachment (not visible in the figure) into which the suction line 3, here a tube, can be fitted. The other end of the tube can be fitted in the suction pump 4. The vacuum or underpressure generated in the suction pump is applied by way of this tube 3 to the breast shield, such that the milk is expressed from the mother's breast and can be collected in the milk collection container 2.

FIG. 1 shows the customary position of use. The first coupling part 12 is directed downward, and the second coupling part 13 is directed rearward or obliquely downward, in any case away from the mother's breast.

All known motor-driven devices can be used as suction pump unit 4. However, a suction pump from the applicant is preferably used which is known by the trade name Symphony. The suction pump unit preferably has actuating buttons and keys 40 and a display 41. In the illustrative embodiment shown here, it is designed as an independent, portable unit. However, it can also be mounted on the breast shield, such that the suction line 3 is dispensed with. Devices of this kind are also available on the market.

According to the invention, on the side of the breast shield 1 a transmission and/or reception unit 5 is now provided which, in this example, has an antenna 50 for transmitting and/or receiving signals. The antenna 50 is shown here protruding from the housing of the unit. However, it can also be arranged within the housing and in particular can have a flat configuration. Instead of a radio antenna, it is also possible to use other means of wireless communication, for example an infrared interface, Bluetooth, optical or acoustic signals, a passive resonance detuning element, RFID, or other known means.

The transmission and/or reception unit 5 has operating keys 51, 52, 53, which are preferably arranged such that they are easy for the mother to reach and actuate, without her having to remove her hand from the breast shield. Instead of the keys, it is also possible to use rotary knobs, inductive touch panels, slides, switches or other operating elements of known types.

Furthermore, the transmission and/or reception unit can be equipped with an optical and/or acoustic display. The display is able to show status information, for example, such as the pump frequency and pump capacity, the selected pump program, or whether in fact a program is being run. It can also display the various options for the suction pump, for example the available pump curve profiles, so as to allow a suitable choice to be made.

The display can also have an acoustic signal transmitter, for example an alarm for indicating incorrect operation of individual elements of the set and/or a sound generator for indicating transmission or reception of signals.

The transmission and reception unit 5 is preferably arranged in the area of the breast shield funnel 10. In the example shown here, it is secured on or recessed in the breast shield neck 11 adjacent to the funnel 10. In the position of use shown here, it is preferably directed upward, such that it can be reached by the same hand with which the mother is holding the breast shield 1 to her breast. However, the unit 5 can also be arranged on the side or bottom of the neck 11, for example.

The unit 5 is secured on or in the breast shield 1 by known means. The main body of the breast shield 1 is itself usually made of plastic and configured in one piece or in several pieces. For example, the unit 5 can be cast into this main body or affixed to it. In the latter case, the main body can have a suitable recess into which the unit 5 can be fitted such that it does not protrude too far and is thus protected. Any cables for signal transmission can be connected to or recessed in the breast shield 1 in the same way.

According to the invention, the unit 5 can be a pure signal transmission unit without a receiving function, a pure signal reception unit without a transmitting function, or a combined signal transmission and reception unit. The suction pump unit preferably also has a signal transmission and/or signal reception unit. Here too, the three abovementioned combinations are possible, and they are intended to lead, in combination with the unit 5, to a functioning unidirectional or bidirectional communication. That is to say, if one is purely a transmitter, the other can receive the signals transmitted by the first one, etc. Of course, the suction pump unit 4 also has an antenna or another suitable interface for wireless communication.

In FIG. 1, the communication is bidirectional. The signals from the side of the breast shield are designated by reference number 8 and the signals from the side of the suction pump are designated by reference number 9.

The following variants are possible in principle, and this applies not just for this illustrative embodiment but also for the examples described hereinafter and for all embodiments according to the invention:

A signal transmission unit for transmitting signals to the suction pump unit can be provided on the side of the breast shield, the signal transmission unit comprising a programming device for manual or automatic programming of the suction pump unit. The programming device preferably transmits a manual pumping procedure to the suction pump unit. It can additionally or instead also transmit a stored pumping procedure to the suction pump unit or activate it in the suction pump unit.

Two pure signal transmission units can be present, a first signal transmission unit being provided on the side of the breast shield and a second signal transmission unit being provided on the side of the suction pump. Suitable signals for displaying information in the area of the breast shield can also be sent for example to data processing units for data evaluation.

A pure signal reception unit can also be arranged in the area of the breast shield, in which case the suction pump unit and/or an external data processing device comprises a suitable transmitter.

The signal unit can have operating means for operating the suction pump, for example in order to switch the pump on and off, to select the frequency, pump capacity or a special pumping program. A manual pump mode or a pump mode programmed by the operating means can be transmitted.

The breastpump can be equipped with a signal transmission unit for transmitting signals to the signal reception unit on the side of the breast shield. The breastpump can be equipped with a signal transmission and signal reception unit for transmitting signals to the signal reception and transmission unit on the side of the breast shield and for receiving signals from the signal reception and transmission unit on the side of the breast shield.

The transmitted information can be, for example, one or more items from the following group: suction frequency, suction capacity, pump program used, pump programs available for selection, pump duration, clock time, filling level in the milk collection container, breast shield temperature, milk flow measurement. Parts of the breast shield can also be controlled or regulated in this way, for example air release valves.

Figure 2:
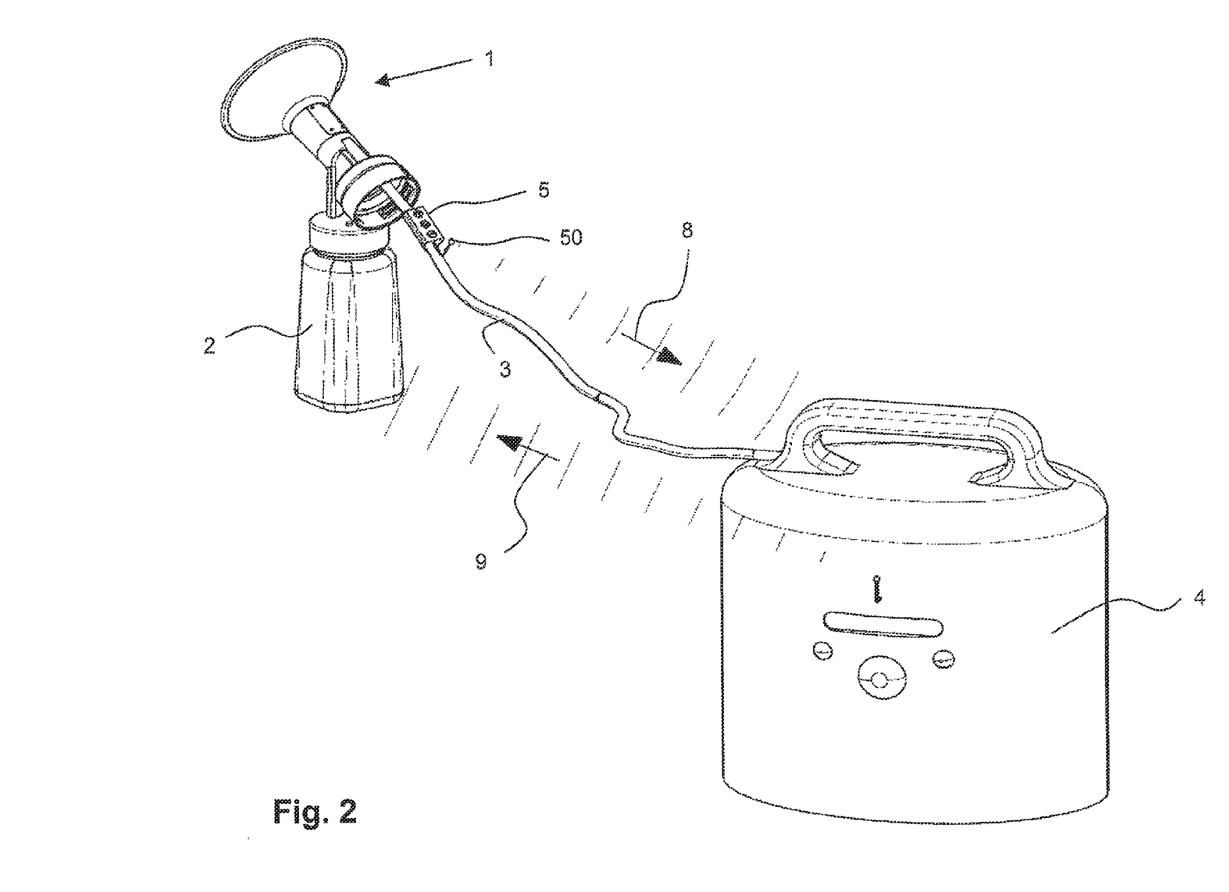
FIG. 2 shows a schematic view of a breastpump set according to a second embodiment of the invention.

FIG. 2 now shows a second illustrative embodiment. Identical parts have been provided with the same reference numbers here and in the following examples, and they are therefore not repeated. The transmission unit and/or reception unit 5 on the side of the breast shield is in this example no longer arranged on the breast shield 1 but on the suction line 3. In another variant, it can also be arranged on a plug connection between breast shield 1 and suction line 3.

Figure 3:
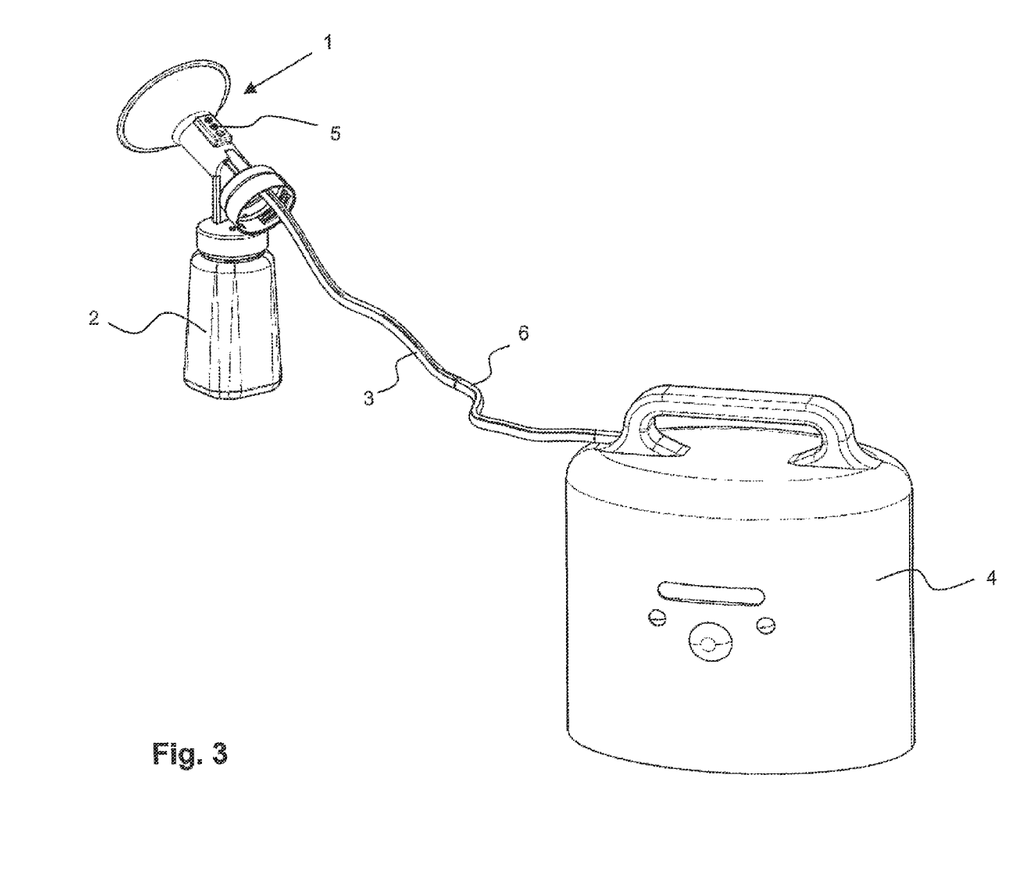
FIG. 3 shows a schematic view of a breastpump set according to a third embodiment of the invention.

In the illustrative embodiment according to FIG. 3, wireless communication has now been replaced by an analog or digital data line 6 for unidirectional or bidirectional transmission of the signals, which data line 6 is preferably secured on the suction line 3.

Figure 4:
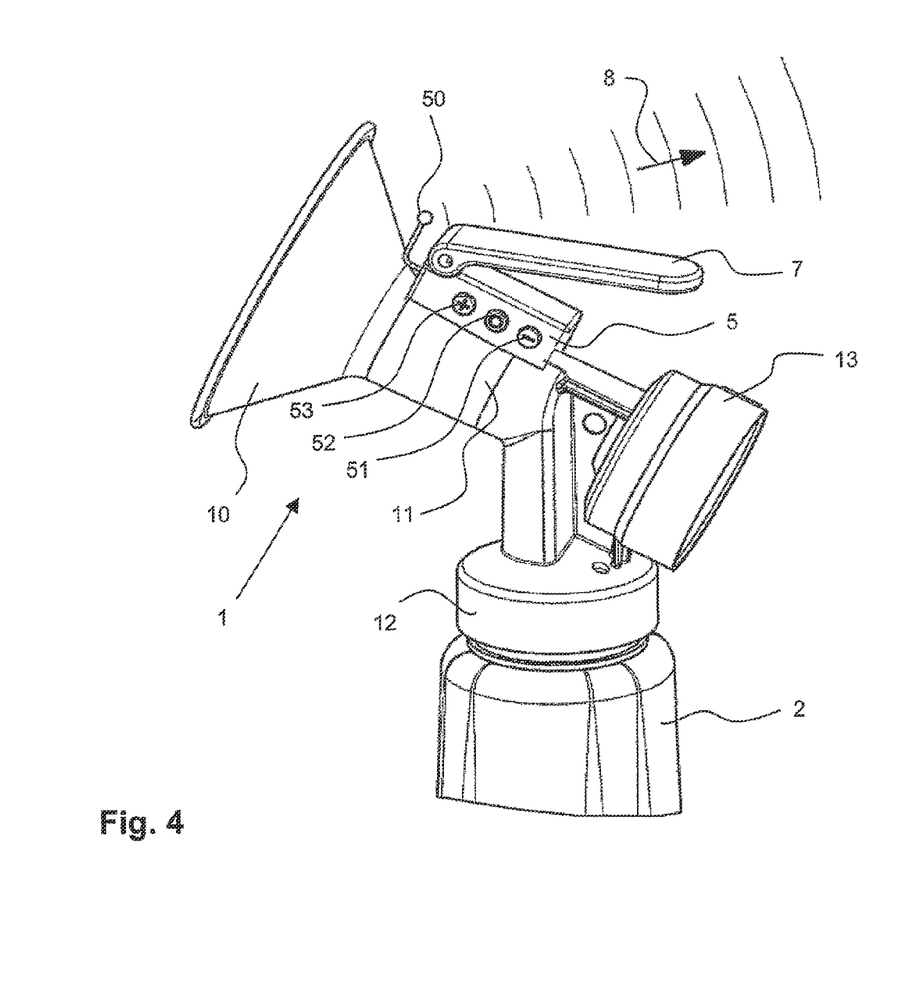
FIG. 4 shows a perspective view of an inventive breast shield according to a fourth embodiment of the invention.

FIG. 4 shows a variant of a breast shield 1 that can be used in all the embodiments. It has an actuating switch or lever 7 with which a pump mode or rhythm (time profile of the vacuum) can be defined manually by the mother, the signals thereof being transmitted to the suction pump unit 4.

Figure 5:
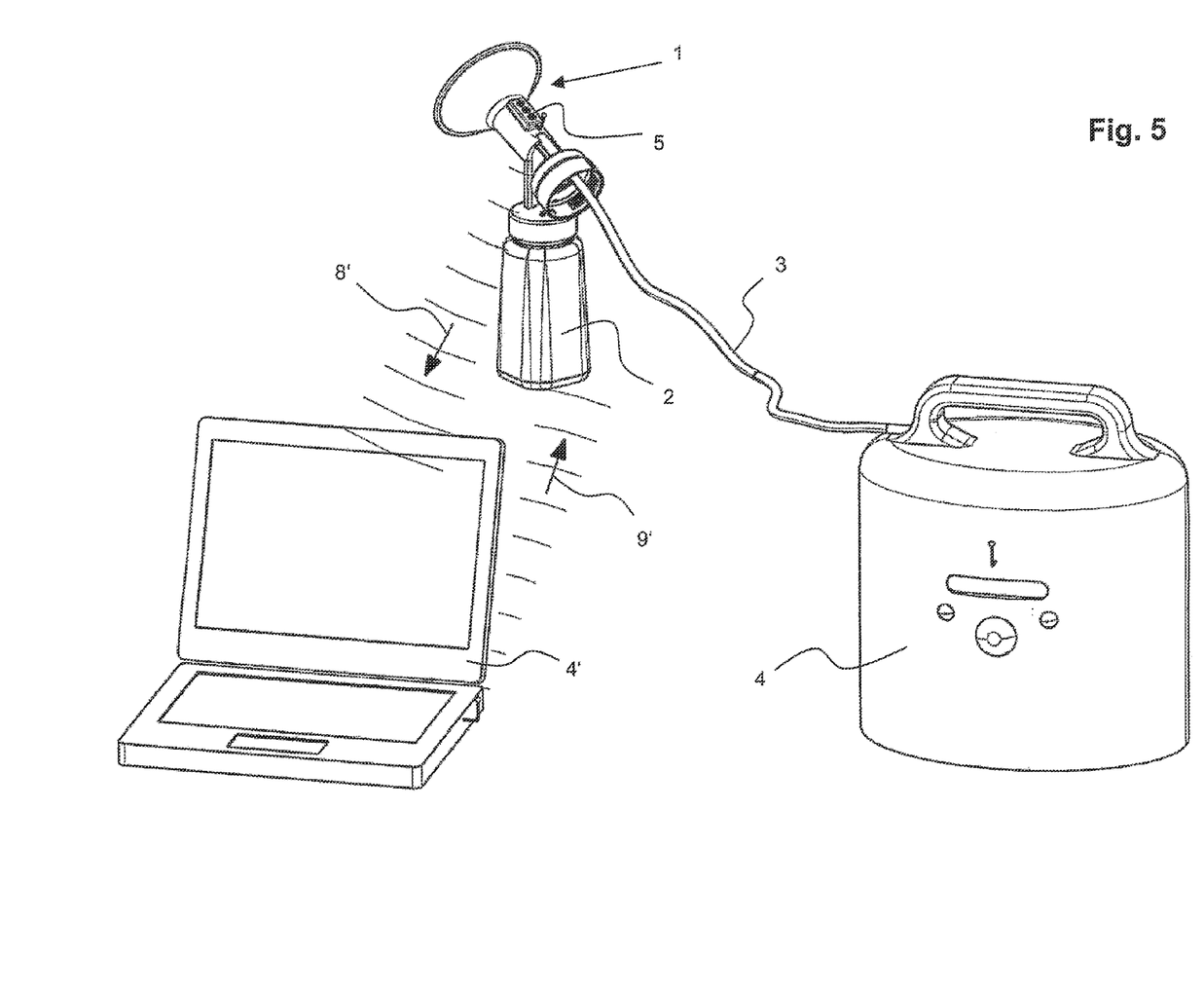
FIG. 5 shows a first variant of the breastpump set according to FIG. 1.

FIG. 5 shows a bidirectional communication 8', 9' with an external device 4', here a computer. The communication could also be unidirectional, however, involving either of the illustrated directions 8', 9'. Instead of the computer, other known devices can also be used, such as a handset, a cellphone, a radio clock, a freely programmable remote control and the like.

Figure 6:
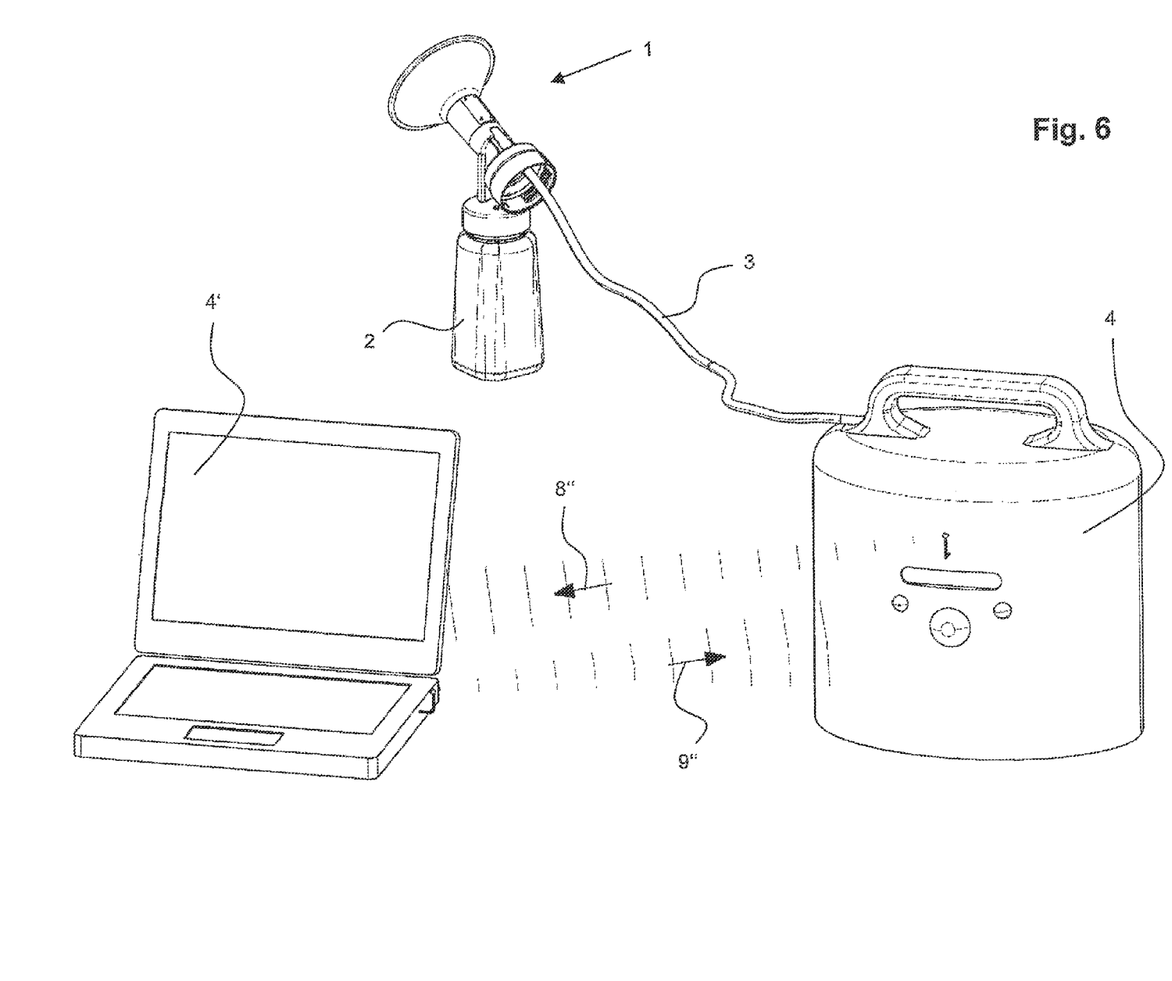
FIG. 6 shows a second variant of the breastpump set according to FIG. 1.

In FIG. 6, the communication 8", 9" takes place between an external device 4' and the suction pump unit 4. Of course, the communications can also take place simultaneously or in succession between external device and breast shield, between external device and suction pump unit, and between breast shield and suction pump unit. The transmission and reception unit 5 is not shown in this figure. It can of course be present or, alternatively, can also be dispensed within the communication between the two abovementioned devices.

The breastpump set according to the invention makes it easier for the mother to operate the pump and breast shield while expressing milk.

LIST OF REFERENCE NUMBERS 1 breast shield
10 breast shield funnel
11 breast shield neck
12 first breast shield coupling part
13 second breast shield coupling part
2 milk collection container
3 suction line
4 suction pump unit
4' computer
40 actuating keys or buttons
41 display
5 transmission and/or reception unit
50 antenna
51 switch-on button
52 first actuating button
53 second actuating button
6 signal line
7 actuating lever
8 breast shield signals
8' breast shield signals
8" suction pump signals
9 suction pump signals
9' computer signals
9" computer signals

The invention claimed is:
1. A breastpump set for expressing human breastmilk, said breastpump set comprising:
at least one breast shield including a funnel adapted to be placed on a mother's breast, and a neck extending from the funnel and connecting to a coupling part for connection to a milk collection container, and
a suction pump unit with an electrically operated suction pump, wherein a first signal transmission unit is provided on the neck or funnel of the breast shield for transmitting signals to the suction pump unit, wherein the signal transmission unit comprises a programming device for manual or automatic programming of the suction pump unit, the programming device being adapted for transmitting a stored pumping procedure to the suction pump unit.

2. The breastpump set according to claim 1, wherein the programming device detects a manual pumping procedure and transmits the manual pumping procedure to the suction pump unit.

3. The breastpump set according to claim 1, wherein the programming device activates a stored pumping procedure in the suction pump unit.

4. The breastpump set according to claim 1, wherein the first signal transmission unit is designed for wireless transmission of signals.

5. A breastpump set according to claim 1,
wherein the breastpump set has a second signal transmission unit provided on the side of the suction pump for transmitting signals to the side of the breast shield.

6. The breastpump set according to claim 5, wherein the first and second signal transmission units are designed for wireless transmission of signals.

7. The breastpump set according to claim 5, wherein the first signal transmission unit is arranged on a plug connection on the side of the breast shield connecting the breast shield to a suction tube between the breast shield and the suction pump, or on the suction tube.

8. A breast shield of a breastpump set for expressing human breastmilk, said breastpump set comprising a suction pump unit with an electrically operated suction pump, wherein the breast shield includes a funnel adapted to be placed on a mother's breast, and a neck extending from the funnel and connecting to a coupling part for connection to a milk collection container, wherein a signal transmission unit is provided on the neck or the funnel of the breast shield for transmitting signals to the suction pump unit, and wherein the signal transmission unit comprises a programming device for manual or automatic programming of the suction pump unit, the programming device being adapted for transmitting a stored pumping procedure to the suction pump unit or for activating a stored pumping procedure in the suction pump unit.

* * * * *